(12) United States Patent
Medford et al.

(10) Patent No.: US 6,887,712 B1
(45) Date of Patent: May 3, 2005

(54) METHODS AND COMPOSITIONS TO LOWER PLASMA CHOLESTEROL LEVELS

(75) Inventors: Russell M. Medford, Atlanta, GA (US); Uday Saxena, Atlanta, GA (US)

(73) Assignee: AtheroGenics, Inc., Alpharetta, GA (US)

( * ) Notice: Subject to any disclaimer, the term of this patent is extended or adjusted under 35 U.S.C. 154(b) by 0 days.

(21) Appl. No.: 09/436,892

(22) Filed: Nov. 9, 1999

Related U.S. Application Data
(60) Provisional application No. 60/107,644, filed on Nov. 9, 1998.

(51) Int. Cl.[7] .............................................. G01N 33/92
(52) U.S. Cl. .................... 436/71; 435/7.1; 435/7.72; 435/7.92; 435/7.94; 436/501; 436/515; 436/523; 436/536; 436/537; 436/546; 436/518; 436/524; 436/528; 436/55; 436/71; 436/164; 436/172; 436/805; 436/815
(58) Field of Search ........................ 435/2, 7.1, 7.6, 435/7.92, 7.8, 7.72, 7.9, 7.94, 7.93; 436/501, 507, 514, 515, 523, 536, 537, 546, 518, 524, 528, 55, 71, 148, 164, 172, 805, 815; 424/9.2; 530/387.3, 388.1, 388.25; 514/548, 712, 824, 825, 826, 855

(56) References Cited

U.S. PATENT DOCUMENTS

| | | | |
|---|---|---|---|
| 4,522,811 A | 6/1985 | Eppstein et al. | |
| 5,155,250 A | 10/1992 | Parker et al. | |
| 5,262,439 A | * 11/1993 | Parthasarathy | ............... 514/548 |
| 5,380,747 A | 1/1995 | Medford et al. | |
| 5,608,095 A | 3/1997 | Parker et al. | |
| 5,750,351 A | 5/1998 | Medford et al. | |
| 5,773,209 A | 6/1998 | Medford et al. | |
| 5,773,231 A | 6/1998 | Medford et al. | |
| 5,792,787 A | 8/1998 | Medford et al. | |
| 5,807,884 A | 9/1998 | Medford et al. | |
| 5,811,449 A | 9/1998 | Medford et al. | |
| 5,846,959 A | 12/1998 | Medford et al. | |
| 5,877,203 A | 3/1999 | Medford et al. | |
| 5,939,424 A | * 8/1999 | Boger et al. | ................. 514/275 |
| 6,027,921 A | * 2/2000 | Heartlein et al. | ........... 435/69.7 |
| 6,107,045 A | * 8/2000 | Koren et al. | .................. 435/7.1 |
| 6,121,319 A | * 9/2000 | Somers | ........................ 514/548 |

FOREIGN PATENT DOCUMENTS

| | | |
|---|---|---|
| FR | 2168137 | 8/1973 |
| WO | WO 94 20083 | 9/1994 |
| WO | WO 95/15760 | 6/1995 |
| WO | WO 95/30415 | 11/1995 |
| WO | WO 97/15546 | 5/1997 |
| WO | WO 98/51289 | 11/1998 |
| WO | WO 98/51662 | 11/1998 |

OTHER PUBLICATIONS

Brown, L., and Langer, R., Transdermal Delivery of Drugs, Annual Review of Medicine, 39:221–229 (1988).
Brown, M.S. and Goldstein, J. L Sci. American (1984) 251, 58–66.
Carew et al. Proc. Natl. Acad. Sci. U.S.A. 84:7725–7729 (1987).
Galeano, N. F.et al., J. Biol. Chem. vo. 269, No. 1, pp. 511–519, 1994.
Goldstein, J.L. and Brown, M.S.: Ann. Rev. Biochem. (1977) 46, 897–930.

(Continued)

*Primary Examiner*—Chris Chin
*Assistant Examiner*—Gailene R. Gabel
(74) *Attorney, Agent, or Firm*—King & Spalding LLP

(57) ABSTRACT

A method is disclosed for determining whether a compound binds to a lipoprotein such as LDL or VLDL in a manner which will lower plasma cholesterol. The method provided includes assessing the ability of the compound to form a complex with the lipoprotein, and then determining whether the newly formed complex causes a change in the structure of apoB-100 that results in increased binding affinity to an LDL receptor.

9 Claims, 6 Drawing Sheets

OTHER PUBLICATIONS

Grundy S.M. New Engl. J. Med. (1988) 319: 24–32.
Grundy S.M., Vega G.L.: Amer J. Med. (1987) 83:9–20.
Innerarity, T., et al., Proc. Natl. Acad. Sci. USA, vol. 84, pp. 6919–6923, 1987.
Yang et al. Nature (1986) 323:734–738.
Milne, R. et al., J. Biol. Chem. vol. 264, No. 33, 1988, pp. 10754–10760.
Milne, R. et al., Arteriosclerosis, vol. 3, No. 1, 1983, pp. 23–30.
Sirtori, C.R., Franceschini G.: Pharmac Ther. (1988) 37:167–191.
Stedronsky ER: Biochim. Biophys. Acta(1994) 1210:255–287.
Wang X, Bucala R, Milne R. Proc. Natl. Acad. Sci (1998) 95:7643–7647.
Weisgraber, K. H., et al., J. Biol. Chem., vol. 258, No. 20, Oct. 25, 1983, pp. 12348–12354.
Wilson M.D., Rudel L.L.: J. Lipid Res. (1994) 35:943–955.
Young, et al. J. Clin. Invest., vol. 79; Jun. 1987, 1831–1841.
W. Frishman, M.Dzimetbaum, P., M.D., and H. Eder, M.D.: Clin. Pharmacol. (1990) 30:3–9.
Knott, TJ, et al. Complete protein sequence and identification of structural domains of human apolopoprotein B, *Nature*, 232, 734–738, 1986.
Yang, C.Y. et al. Sequence, structure, receptor–binding domains and internal repeats of human apolipoprotein B–100 *Nature* 323, 738–742 (1986).

* cited by examiner

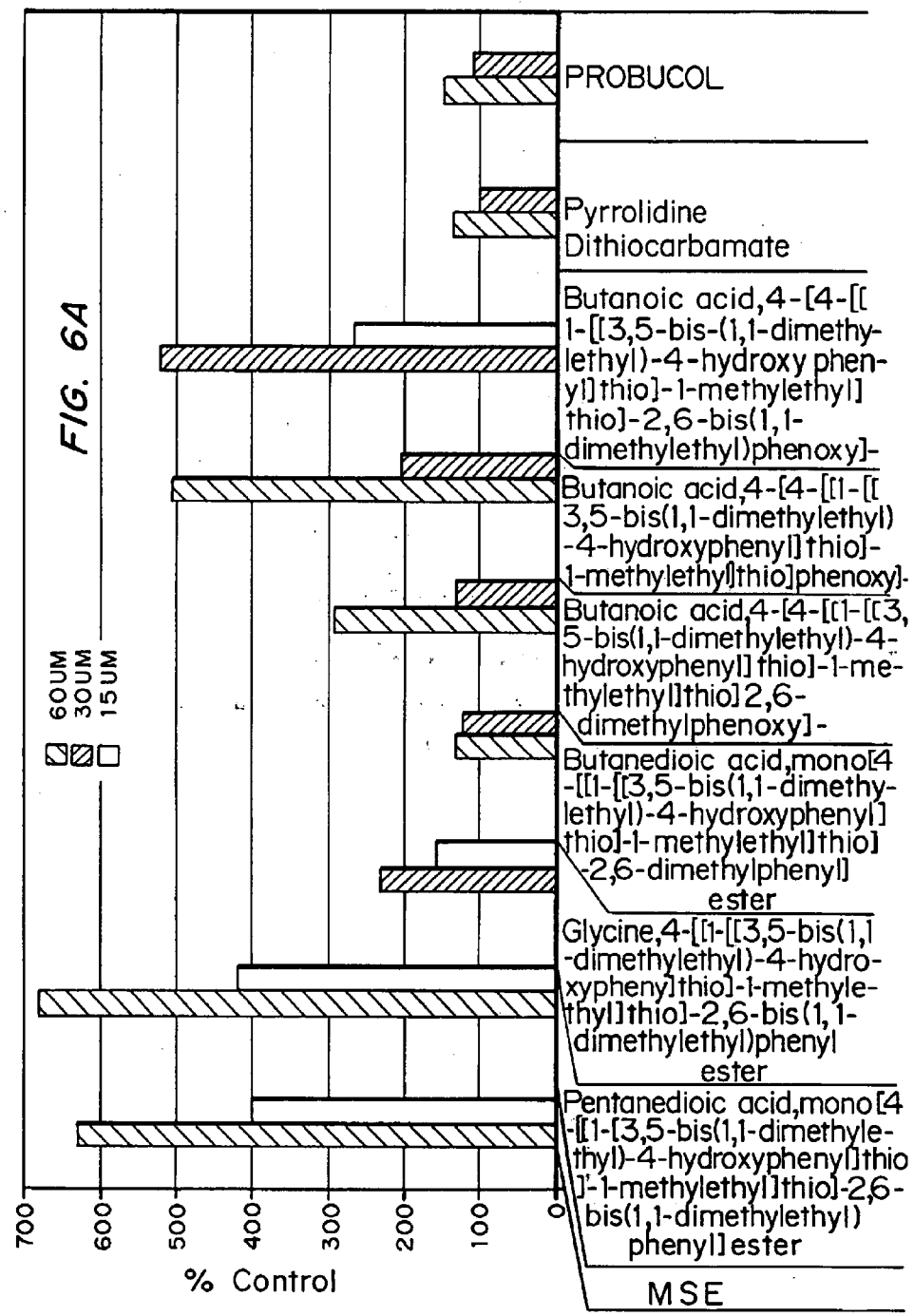

METHODS AND COMPOSITIONS TO LOWER PLASMA CHOLESTEROL LEVELS

This application claims priority to U.S. provisional application No. 60/107,644, filed on Nov. 9, 1998.

This invention is in the area of methods and compositions to lower plasma cholesterol levels by lowering the levels of circulating low density lipoproteins (LDL) and very low density lipoproteins (VLDL).

BACKGROUND OF THE INVENTION

Coronary heart disease (CHD) remains the leading cause of death in the industrialized countries. The primary cause of CHD is atherosclerosis, a disease characterized by the deposition of lipids, including cholesterol, in the arterial vessel wall, resulting in a narrowing of the vessel passages and ultimately hardening the vascular system.

It is now well accepted that atherosclerosis can begin with local injury to the arterial endothelium followed by proliferation of arterial smooth muscle cells from the medial layer to the intimal layer along the deposition of lipid and accumulation of foam cells in the lesion. As the atherosclerotic plaque develops it progressively occludes more and more of the affected blood vessel and can eventually lead to ischaemia or infarction. Since deposition of circulating lipids such as cholesterol plays a major role in the initiation and progression of atherosclerosis, it is important to identify methods and compositions to lower circulating cholesterol levels.

Circulating lipoproteins serve as vehicles for the transport of insoluble lipids like cholesterol esters, triglycerides and the more polar phospholipids and unesterified cholesterol in the aqueous environment of plasma (Bradely, W. A. and Gotto, A. M.: American Physiological Society, Bethesda, Md., (1978) pp 117–137). The solubility of these lipids is achieved through physical association with proteins termed as apolipoproteins and the lipid-protein complexes are called lipoproteins (Dolphin, P. J.: Can. J. Biochem. Cell. Biol. (1985) 63, 850–869). Five distinct classes of lipoproteins, chylomicrons, very low density lipoproteins (VLDL), low density lipoproteins (LDL), high density lipoproteins (HDL) and LP(a), have been isolated from human plasma (Alaupovic, P.: In Handbook of Electrophoresis. (1980) Vol. 1, pp. 27–46, Havel, R. J., Eder, H. A. and Bragdon, J. H.: J. Clin. Invest. (1955) 34, 1343–1353). LDL is the major carrier of cholesterol in human plasma.

Dietary triglycerides and cholesterol are assembled by enterocytes (intestinal cells) into a chylomicron particle, which enters circulation through the lymphatic system (Brown, M. S. and Goldstein, J. L Sci. American (1984) 251, 58–66). Chylomicrons provide fatty acids to peripheral cells and cholesterol to liver. The liver in turn repackages cholesterol together with triglycerides into another lipoprotein called VLDL.

The function of VLDL is similar to chylomicrons, i.e. supply of free fatty acids to the muscle and adipose tissues and cholesterol to peripheral cells (Brown, M. S. and Goldstein, J. L Sci. American (1984)251, 58–66). In the circulatory system, triglycerides in the VLDL particle are hydrolyzed by an enzyme called lipoprotein lipase (LPL) and additional processing by hepatic lipase finally converts it to LDL (Dolphin, P. J.: Can. J. Biochem. Cell. Biol. (1985) 63, 850–869). Thus, the liver produces VLDL, the precursor of LDL. Because VLDL is a precursor to LDL, decreases in VLDL production translate into lowered LDL levels. High levels of circulating LDL have been positively correlated with the development of coronary disease. While LDL cholesterol is clearly an independent positive risk factor, HDL cholesterol is considered to be a negative risk factor (D. L. Tribble, R. M. Krauss. Advances in Internal Medicine. (1993) 38:1–29).

Apoprotein B

Apoprotein B-100 (apoB) is the major apoprotein of LDL and its ligand for the LDL receptor. ApoB-100 is a large protein with a molecular weight (MW) of 549,000. The protein is highly hydrophobic and is insoluble in the absence of lipids. The structure of apoB-100 has been studied using monoclonal antibodies raised to specific regions (antigenic regions or epitopes) on the protein. These monoclonal antibodies have been used to "map" the site on apoB-100, which binds to the LDL receptor. Mapping the various epitopes on apoB in VLDL and LDL using monoclonal antibodies has been a productive method to understand the role of various portions of this protein in lipoprotein uptake. Changes in the immunoreactivity of the epitopes on apoB to monoclonal antibodies have shown correlation with the uptake of LDL by cells in culture (N. F. Galeano, et al., J. Biol. Chem. vo. 269, no. 1, pp. 511–519, 1994).

Monoclonal antibodies have been used to bind to epitopes of a known region of apoB in order to determine the binding region for LDL receptor (Milne, R. et al., J. Biol. Chem. vol. 264, no. 33, 1988, pp. 10754–60; Milne, R. et al., Arteriosclerosis, vol. 3, no. 1, 1983, pp. 23–30). Assessment of the epitope position for the receptor blocking monoclonal antibodies can be used to predict the extent of the LDL receptor binding region of apoB (Pease, R., et al., J. Biol. Chem. vol. 266, no. 1, 1990, pp. 553–68).

Apolipoprotein E

Apolipoprotein E (apoE), like apoB, binds to the LDL receptors and is capable of transporting cholesterol throughout the system. ApoE mediates the transport and uptake of cholesterol and lipid by its high affinity binding with the LDL receptor. The LDL receptor recognizes both apoB and apoE with comparable affinity (Wilson, C., et al., Science vol. 252 pp. 1817–1822, 1991). The receptor binding domain of the apoE protein has been characterized via inhibition studies which utilized monoclonal antibodies (Weisgraber, K. H., et al., J. Biol. Chem., vol. 258, No. 20, Oct. 25, 1983, pp. 12348–12354). Further, the three-dimensional structure of the LDL receptor binding domain of apoE has been determined by x-ray crystallography (Wilson, C., et al., Science vol. 252 pp. 1817–1822, 1991).

Clearance of LDL from Circulation

LDL is removed from plasma by a high affinity receptor called the LDL receptor, present on the cell-surface of peripheral and liver cells (Goldstein, J. L. and Brown, M. S.: Ann. Rev. Biochem. (1977) 46, 897–930). This receptor-mediated pathway accounts for uptake and degradation of LDL by cells, and in the process, cholesterol is delivered to these cells. Thus uptake of LDL by the receptor mediated process permits cells to acquire cholesterol from the lipoprotein, and this in turn provides cholesterol for membrane synthesis in all tissues and steroid hormone synthesis in the adrenal, ovaries and testes.

Uptake by the LDL receptor pathway is the major mechanism of LDL clearance from the plasma. This process of lipoprotein uptake is a highly coordinated and orchestrated process dictated by apolipoprotein composition and lipid content of the lipoprotein. The apolipoprotein on LDL, called apoB-100, mediates the interaction of LDL with the LDL receptor. Specific amino acid sequences on apoB form the binding site for apoB to the cell-surface LDL receptors (Knott et al., Nature (1986) 323:734–738).

Besides LDL, VLDL can also bind to the LDL receptors since it contains apoB-100 as well as apoE, another apolipoprotein, which contains LDL-receptor recognizable amino acid sequences. It is well recognized that VLDL are heterogeneous with respect to size and composition, and each subclass of VLDL differ in their ability to interact with the LDL receptor. For example, the large sized VLDL do not normally bind to the LDL receptor even though they contain apoB-100 and apoE. Only smaller VLDL bind to the receptor. It is suggested that both apoB-100 and apoE in the large VLDL do not possess the appropriate three dimensional structure for receptor recognition. Similarly, certain types of LDL, for example those found in the diabetic plasma (glycosylated LDL) and oxidized LDL, also do not bind LDL receptors because of incorrect structure of apoB-100 (Wang X, Bucala R, Milne R. Proc. Natl. Acad. Sci (1998) 95:7643–7647). Thus besides the amino acid sequence requirement, there is also a strict structural requirement of apoB-100 for optimal LDL binding by the LDL receptor.

The significance of apoB and apoE receptors in LDL clearance is demonstrated by patients possessing a genetic predisposition to coronary disease. A condition known as familial hypercholesterolemia (FH) impairs the clearance of LDL from blood plasma in patients lacking apoB or apoE LDL-receptors or having defective apoB or apoE LDL-receptors (Innerarity, T., et al., Proc. Natl. Acad. Sci. USA, vol. 84, pp. 6919–23, 1987). At least one abnormal apoB species has been reported in humans. Young, et al. documented the existence of one such abnormal apoB protein, apoB-37 (J. Clin. Invest., Vol. 79, June 1987, 1831–1841). This abnormal protein was found to occur frequently in individuals suffering from a form of familial hypobetalipoproteinemia, with the abnormal protein coding alleles being inherited and traced through over three generations of an affected family.

Existing Lipid Lowering Therapies

Diet contributes up to 40% of cholesterol that enters through the intestine and bile contributes the rest of the "exogenous" cholesterol absorbed through the intestine (Wilson M. D., Rudel L. L.: J. Lipid Res. (1994) 35:943–955). Decreasing dietary cholesterol absorption therefore is a regulatory point for cholesterol whole body homeostasis. Cholesterol absorption inhibitors lower plasma cholesterol by reducing the absorption of dietary cholesterol in the gut or by acting as bile acid sequestrants (Stedronsky E R: Biochim. Biophys. Acta(1994) 1210:255–287).

Since it has been determined that hypercholesterolemia is due to elevated LDL (hyperlipidemia), the lowering of LDL levels by drug therapy is attempted. There are several drug classes that are commonly used to lower LDL levels, including bile acid sequestrants, nicotinic acid (niacin), and 3-hydroxy-3-methylglutaryl coenzyme A (HMG CoA) reductase inhibitors. Probucol and the fibrate derivatives are sometimes used as adjunctive therapy, usually in combination with other medications.

Cholesterol lowering agents decrease total plasma and LDL cholesterol and may increase HDL. Neomycin, a non-absorbable aminoglycoside binds dietary cholesterol and prevents intestinal absorption. Another drug in this category is cholestyramine. Cholestyramine is an anion-exchange resin, which acts by binding bile acids within the intestinal lumen, thus interfering with their reabsorption and enhancing fecal excretion. Cholesterol-lowering agents in this class require large dosage and are usually associated with poor compliance and malabsorption of other nutrients and drugs.

Important classes of drugs that act on liver are fibrates. Fibrates are fibric acid derivatives (bezafibrate, fenofibrate, gemfibrozil, and clofibrate) which profoundly lower plasma triglyceride levels and elevate HDL (Sirtori C. R, Franceschini G.: Pharmac Ther. (1988) 37:167–191; and Grundy S. M., Vega G. L.: Amer J. Med. (1987) 83:9–20). The typical clinical use of fibrates is in patients with hypertriglyceridemia, low HDL and combined hyperlipidemia.

The mechanism of action of fibrates is not completely understood but involves the induction of certain apolipoproteins and enzymes involved in VLDL and HDL metabolism. Patient compliance with fibrates is good, but they are not drugs of choice for lowering LDL cholesterol. Nicotinic acid (niacin), a water-soluble vitamin has a lipid lowering profile similar to fibrates and may target the liver.

Statins represent a class of compounds which are inhibitors of HMG CoA reductase, a key enzyme in the cholesterol biosynthetic pathway (Endo A, In: Cellular Metabolism of the Arterial Wall and Central Nervous System. Selected Aspects. Schettler G, Greten H, Habenicht AJR(Eds.) Springer-Verlag, Heidelberg (1993)).

The statins decrease liver cholesterol biosynthesis, which increases the production of LDL receptors thereby decreasing plasma total and LDL cholesterol (Grundy S. M. New Engl. J. Med. (1988) 319:24–32 and Endo A: J. Lipid Res. (1992) 33: 1569–1582). Depending on the agent and the dose used, statins may decrease plasma triglyceride levels and may increase HDL. Currently the statins on the market are Lovastatin (Merck), Simvastatin (Merck), Pravastatin (Sankyo and Squibb) and Fluvastatin (Sandoz). A fifth statin, Atorvastatin (Parke-Davis/Pfizer), is the most recent entrant into the statin market. Statins have become the standard therapy for LDL cholesterol lowering. The statins are effective LDL lowering agents but have side effects, the most common being increases in serum enzymes (transaminases and creatinine kinase). In addition, these agents may also cause myopathy and rhabdomyolysis especially when combined with fibrates.

Another drug that in part may impact the liver is probucol (P. Zimetbaun, M.D., H. Eder, M.D., and W. Frishman, M.D.: Clin. Pharmacol. (1990) 30:3–9). Probucol is used primarily to lower serum cholesterol levels in hypercholesterolemic patients and is commonly administered in the form of tablets available under the trademark Lorelco™. Probucol is chemically related to the widely used food additives 2,[3]-tert-butyl-4-hydroxyanisole (BHA) and 2,6-di-tert-butyl-4-methyl phenol (BHT). Its full chemical name is 4,4'-(isopropylidenedithio) bis(2,6-di-tert-butylphenol). Probucol is a lipid soluble agent used in the treatment of hypercholesterolemia including familial hypercholesterolemia (FH). Probucol reduces LDL cholesterol typically by 10% to 20% but also reduces HDL by 20% to 30%. The drug has no effect on plasma triglycerides. The mechanism of action of probucol in lipid lowering is not completely understood. The LDL lowering effect of probucol may be due to decreased production of apoB containing lipoproteins and increased clearance of LDL. Probucol lowers LDL in the LDL-receptor deficient animal model (WHHL rabbits) as well as in FH populations. Probucol has been shown to actually slow the progression of atherosclerosis in LDL receptor-deficient rabbits as discussed in Carew et al. Proc. Natl. Acad. Sci. U.S.A. 84:7725–7729 (1987). The HDL lowering effect of probucol may be due to decreased synthesis of HDL apolipoproteins and increased clearance of this lipoprotein. High doses of probucol are required in clinical use.

U.S. Pat. No. 5,262,439 to Parthasarathy discloses analogs of probucol with increased water solubility in which one or both of the hydroxyl groups are replaced with ester groups that increase the water solubility of the compound. In one embodiment, the derivative is selected from the group consisting of a mono- or di-probucol ester of succinic acid, glutaric acid, adipic acid, seberic acid, sebacic acid, azelaic acid, or maleic acid. In another embodiment, the probucol derivative is a mono- or di-ester in which the ester contains an alkyl or alkenyl group that contains a functionality selected from the group consisting of a carboxylic acid group, amine group, salt of an amine group, amide groups, amide groups, and aldehyde groups.

WO 98/09773 filed by AtheroGenics, Inc. discloses that monoesters of probucol, and in particular, the monosuccinic acid ester of probucol, are effective in simultaneously reducing cholesterol, lowering LDL, and inhibiting the expression of VCAM-1, and thus these compounds are useful as composite cardiovascular agents. Since the compounds exhibits three important vascular protecting activities simultaneously, the patient can take one drug instead of multiple drugs to achieve the desired therapeutic effect.

WO 98/09781 discloses therapeutic agents for the treatment of diseases, including cardiovascular diseases, that are mediated by VCAM-1.

U.S. Pat. No. 5,807,884 claims a method for treating a disease (including a cardiovascular disease) mediated by VCAM-1 that includes administering a substance that inhibits the oxidation of a polyunsaturated fatty acid.

U.S. Pat. No. 5,811,449 covers the method for the treatment of cardiovascular disease that includes suppressing the expression of a redox-sensitive gene selected from the group consisting of MCP-1, IL-6 and thrombin receptor that includes administering an effective amount of a substance that prevents or minimizes the oxidation of a polyunsaturated fatty acid.

U.S. Pat. No. 5,846,959 claims a method for treating a cardiovascular disease mediated by VCAM-1 expression, that includes administering an effective amount of a substance which inhibits the oxidation of a polyunsaturated fatty acid in combination with another cardiovascular drug selected from the group consisting of lipid lowering agents, platelet aggregation inhibitors, antithrombotic agents, calcium channel blockers, angiotensin converting enzyme inhibitors, and β-blockers.

U.S. Pat. No. 5,750,351 claims a method to assess a test compound for its ability to treat a disorder mediated by VCAM-1 that includes evaluating the ability of the compound to inhibit the oxidation of a polyunsaturated fatty acid.

U.S. Pat. No. 5,773,209 claims a method for the prediction or assessment of redox-sensitive gene mediated disease in vivo, that includes quantifying the level of oxidized polyunsaturated fatty acid in the tissue or blood, or a mediator of inflammation that is induced by polyunsaturated fatty acid or an oxidized polyunsaturated fatty acid.

U.S. Pat. No. 5,773,231 claims a method for the evaluation of the sensitization of a host's vascular endothelial cells to polyunsaturated fatty acids or their oxidized counterparts, that includes challenging a host with a polyunsaturated fatty acid or oxidized polyunsaturated fatty acid and comparing to a population norm the resulting concentration of VCAM-1 or other mediator of inflammation expressed by a redox-sensitive gene on exposure to the polyunsaturated fatty acid or oxidized fatty acid.

U.S. Pat. Nos. 5,380,747 and 5,811,449 claim a method for the treatment of cardiovascular disease in humans that includes administering an effective amount of a dithiocarbamate of defined structure. U.S. Pat. No. 5,792,787 discloses a method for the suppression of VCAM-1 expression in humans that includes administering an effective amount of a dithiocarbamate of defined structure.

U.S. Pat. No. 5,877,203 directed to a method for treating inflammatory diseases by suppressing VCAM-1 expression in humans that includes administering a dithiocarbamate of defined structure.

A series of French patents disclose that certain probucol derivatives are hypocholesterolemic and hypolipemic agents: Fr 2168137 (bis 4-hydroxyphenylthioalkane esters); Fr 2140771 (tetralinyl phenoxy alkanoic esters of probucol); Fr 2140769 (benzofuryloxyalkanoic acid derivatives of probucol); Fr 2134810 (bis-(3-alkyl-5-t-alkyl-4-thiazole-5-carboxy)phenylthio)alkanes; FR 2133024 (bis-(4-nicoinoyloxyphenylhio)propanes; and Fr 2130975 (bis(4-(phenoxyalkanoyloxy)-phenylthio)alkanes).

U.S. Pat. No. 5,155,250 discloses that 2,6-dialkyl-4-silylphenols are antiatherosclerotic agents. The same compounds are disclosed as serum cholesterol lowering agents in PCT Publication No. WO 95/15760, published on Jun. 15, 1995. U.S. Pat. No. 5,608,095 discloses that alkylated-4-silyl-phenols inhibit the peroxidation of LDL, lower plasma cholesterol, and inhibit the expression of VCAM-1, and thus are useful in the treatment of atherosclerosis.

Since cardiovascular disease is the leading cause of death in North America, there is a need to provide new therapies for its treatment, especially those that work through a mechanism different from the current drugs and can be used in conjunction with them.

It is therefore an object of the present invention to provide a new method to lower plasma cholesterol, and in particular low density lipoproteins and very low density lipoproteins.

It is another an object of the present invention to provide an assay to assess the effectiveness of the new method to lower plasma cholesterol.

SUMMARY OF THE INVENTION

It has been discovered that plasma cholesterol can be lowered by administration of a compound that binds to cholesterol-carrying lipoprotein (e.g. LDL or VLDL) in a manner that alters the three dimensional configuration of the lipoprotein and increases the binding affinity of the apoB-100 protein to the LDL receptor, including those on the surface of hepatic cells. Such compounds are referred to herein as "LDL clearance enhancing drugs." By increasing the binding affinity of the lipoprotein to LDL receptor, the LDL clearance enhancing drug causes the lipoprotein to be removed (i.e., cleared) from the plasma more effectively, which lowers the plasma cholesterol level. Therefore, in a first embodiment of the invention, a method for lowering cholesterol in a host in need thereof, including a human, is provided that includes the administration of an effective amount of a compound which binds to cholesterol-carrying lipoprotein (e.g. LDL or VLDL) in a manner that alters the three dimensional configuration of the lipoprotein and increases the binding affinity of the apoB-100 protein to the LDL receptor, including those on the surface of a hepatic cell. According to this invention, one can determine whether a compound is an LDL clearance enhancing drug using any of the methods described herein, including mixing the drug with cholesterol-containing lipoprotein in vivo or in vitro, isolating the complex, and determining whether the binding of the complex causes a change in the three dimensional conformation of apoB-100 in the lipoprotein that enhances the binding affinity of the lipoprotein to the LDL receptor. In one aspect of this first embodiment, the LDL-clearance enhancing drug is not probucol or a mono- or di-ester of probucol. In another aspect of this first embodiment, the clearance enhancing drug is not a compound described in WO 98/09773. In yet another aspect of this first embodiment, the LDL-clearance enhancing drug is not a silyl compound described in U.S. Pat. Nos. 5,155,250 or 5,608,095.

In another embodiment of the invention, an assay for determining whether a compound binds to a lipoprotein such as LDL or VLDL in a manner which will lower plasma cholesterol is provided that includes assessing the ability of the compound to form a complex with the lipoprotein, e.g., LDL or VLDL, and then determining whether the newly formed complex causes a change in the structure of apoB-100 that results in increased binding affinity to the LDL receptor.

As one nonlimiting example of this embodiment, the test compound can be fed to a host animal, for example a rabbit, together with a high-fat diet for six weeks at a suitable dosage orally. The animals are then bled, preferably at six weeks, and plasma lipoproteins isolated using high speed ultra-centrifugation. The amount of test compound bound to each of the lipoproteins is then estimated. To determine if the bound test compound causes a change in the structure of apoB-100 that would be therapeutically useful, a sandwich immunoreactivity assay is provided which measures the presentation of a specific epitope known to be important to the binding of apoB-100 to the LDL receptor. The sandwich ELISA utilizes an antibody, preferably a monoclonal antibody described in more detail below, directed to the specified epitope on apoB-100 as a capture antibody laid onto a microtitre plate. LDL added to the plate is bound to the antibody as a result of recognition of the specific epitope. A second antibody, which can be polyclonal or monoclonal, is then used to quantify the amount of LDL captured.

In another aspect of the invention, using agarose electrophoresis or another suitable technique, changes in the electrophorectic mobility pattern of LDL or VLDL complexed with the test compound is assessed to investigate the interaction between the test compound and the lipoprotein. If the electrophorectic mobility is altered, or if by some other assessment, it is determined that the compound binds to the lipoprotein and alters the three dimensional configuration of the structure, then using another approach, including but not limited to reaction with a monoclonal antibody targeted to an important epitope in apoB-100, one can determine whether and to what extent the compound enhances or diminishes the binding of apoB-100 to the LDL receptor for cholesterol clearance.

It has been discovered that the monosuccinic acid ester of probucol (MSE) strongly binds to serum LDL and VLDL, causing a change in the conformation of the apoB-100 protein which increases the binding of the lipoprotein to hepatic LDL receptors.

BRIEF DESCRIPTION OF THE DRAWINGS

FIG. 6a is a graph that demonstrates the increased binding of LDL to the capture monoclonal antibody for the monosuccinic acid ester of probucol and several other probucol derivatives.

DETAILED DESCRIPTION OF THE INVENTION

Figure 1:
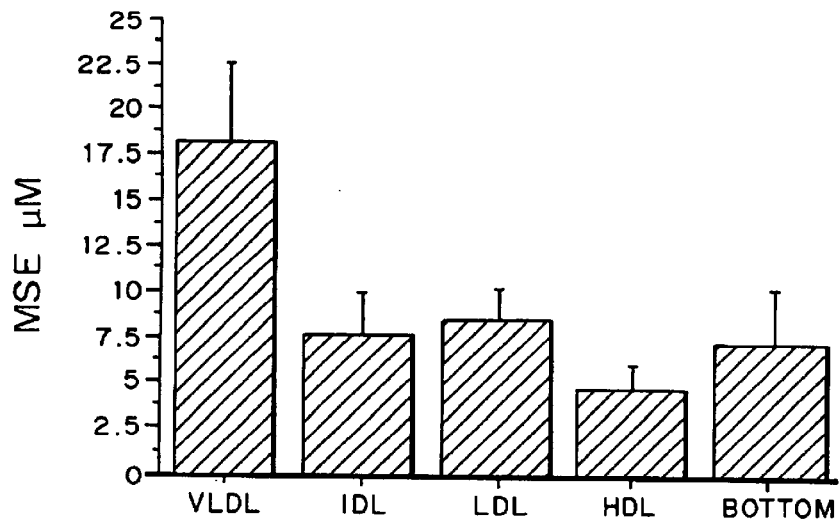
FIG. 1 is a bar graph of the distribution of the monosuccinic acid ester ("MSE") of probucol in circulating lipoproteins.

It has been discovered that plasma cholesterol can be lowered by administration of a compound that binds to cholesterol-carrying lipoprotein (e.g. LDL or VLDL) in a manner that alters the three dimensional configuration of the lipoprotein and increases the binding affinity of the apoB-100 protein to the LDL receptors on the surface of hepatic cells. Such compounds are referred to herein as "LDL clearance enhancing drugs." By increasing the binding affinity of the lipoprotein to the hepatic LDL receptors, the lipoprotein is removed (i.e., cleared) from the plasma more effectively and the plasma cholesterol level is lowered. Therefore, in a first embodiment of the invention, a method for lowering cholesterol in a host in need thereof, including a human, is provided that includes the administration of an effective amount of a compound which binds to cholesterol-carrying lipoprotein (e.g. LDL or VLDL) in a manner that alters the three dimensional configuration of the lipoprotein and increases the binding affinity of the apoB-100 protein to the LDL receptors on the surface of hepatic cells. According to this invention, one can determine whether a compound is an LDL clearance enhancing drug using any of the methods described herein, including mixing the drug with cholesterol-containing lipoprotein in vivo or in vitro, isolating the complex, and determining whether the binding of the complex causes a change in the three dimensional conformation of apoB-100 in the lipoprotein that enhances the binding affinity of the lipoprotein to the LDL receptor. In one aspect of this first embodiment, the LDL-clearance enhancing drug is not probucol or a mono- or di-ester of probucol. In another aspect of this first embodiment, the clearance enhancing drug is not a compound described in WO 98/09773. In yet another aspect of this first embodiment, the LDL-clearance enhancing drug is not a silyl compound described in U.S. Pat. No. 5,155,250 or 5,608,095.

If a host exhibiting a high plasma cholesterol level is given a compound which has been identified as a LDL clearance enhancing drug, and that host is nonresponsive to therapy, then the possibility exists that the host has a high cholesterol level because the host's apoB-100 protein is genetically diverse or altered in such a manner that it cannot not present the LDL-receptor epitope in an effective manner.

Therefore, the invention includes a method to assess whether a host has a variant of apoB-100 that when complexed in a lipoprotein, has a decreased ability to bind to a LDL receptor (which results in naturally high LDL or VLDL cholesterol levels) that includes monitoring the response of the host to a LDL clearance drug, confirming that the patient has a lower than normal response to the drug, and then isolating and evaluating the host's apoB-100 protein for variations that result in decreased binding to the LDL receptor.

In another embodiment of the invention, a method for determining whether a compound binds to LDL or VLDL in a manner which will lower plasma cholesterol is provided that includes assaying the ability of the compound to form a complex with LDL or VLDL and then assessing whether the newly formed complex causes a change in the structure of apoB-100 that results in increased binding affinity to the LDL receptor.

In summary, the invention includes the following embodiments:

(i) A method to assess whether a compound is an LDL clearance enhancing drug that includes mixing the drug with cholesterol-containing lipoprotein in vivo or in vitro; isolating the complex, and determining whether the binding of the compound to the complex causes a change in the three dimensional conformation of apoB-100 in the lipoprotein that enhances the binding affinity of the lipoprotein to the LDL receptor;

(ii) A method for lowering plasma cholesterol in a host, comprising administering to the host a compound that form a complex with cholesterol-containing lipoprotein, e.g., LDL or VLDL and then assessing whether the newly formed complex causes a change in the structure of apoB-100 that results in increased binding affinity of the lipoprotein to the LDL receptor;

(iii) A method to alter the conformation of a cholesterol-containing lipoprotein that includes mixing the cholesterol-containing lipoprotein in vivo or in vitro with a compound and determining whether the binding of the compound to the complex causes a change in the three dimensional conformation of apoB-100 in the lipoprotein that enhances the binding affinity of the lipoprotein to an LDL receptor;

(iv) A method to determine whether a high plasma cholesterol level in a host is due to a genetic alteration of the host's apoB-100 protein that includes administering a LDL clearance enhancing drug to the patient, observing a lower than normal decrease in plasma cholesterol level, and then isolating and evaluating the host's apoB-100 protein;

(v) A method to determine whether a high plasma cholesterol level in a host is due to a genetic alteration of the host's apoB-100 protein that includes exposing the host's apoB-100 protein to an LDL clearance enhancing drug in vitro under conditions in which the host's apoB-100 protein and the drug can form a complex, and then isolating and evaluating the change in conformation of the host's apoB-100 protein caused by any complexation.

(vi) A method to determine if a compound causes a change in the structure of apoB-100 in a cholesterol-containing lipoprotein that would be therapeutically useful, comprising carrying out a sandwich immunoreactivity assay in which an antibody, preferably a monoclonal antibody, directed to an epitope on apoB-100 (known to be important to the LDL receptor binding process) as a capture antibody is laid onto a plate, the cholesterol-containing lipoprotein/test compound complex is added to the plate, and a second antibody, which can be polyclonal or monoclonal, is then used to quantify the amount of LDL complex captured; and (vii) A method to assess a conformational change in cholesterol-containing lipoprotein caused by complexation with a test compound that includes assessing the change in the electrophorectic mobility pattern of the cholesterol-containing lipoprotein using electrophoresis.

I. LDL Clearance Enhancing Drugs

It has been discovered that the monosuccinic acid ester of probucol (MSE) strongly binds to serum LDL and VLDL, causing a change in the conformation of the apoB-100 protein which increases the binding of the lipoprotein to hepatic LDL receptors. The use of the monosuccinic acid ester of probucol to treat cardiovascular disease is described generally in U.S. Pat. No. 5,262,439; WO98/09773 and WO98/09781. None of these patent specifications teach that MSE binds to LDL or VLDL in a manner that increases the binding of the complexed apoB-100 protein to the LDL receptor for enhanced plasma cholesterol clearance. Monosuccinic acid ester of probucol is used in this specification as a prototype LDL clearance enhancing drug and in illustrations of how to assess the ability of a drug to bind LDL in a manner that increases the binding of apoB-100 to the LDL receptor on the surface of hepatic cells. Given its exemplification, one of ordinary skill can easily assess whether other drugs act in a similar manner to increase binding of apoB-100 to the LDL receptor.

It has been discovered that some probucol derivatives, particularly the monosuccinic acid ester of probucol, significantly enhance the clearance of VLDL, even though probucol itself has little effect. It has been demonstrated that probucol decreases serum cholesterol in LDL-receptor knockout (i.e., deficient) mice, which provides evidence that probucol does not lower cholesterol substantially through an interaction with LDL-receptor. In contrast, MSE exhibits little or no effect on serum cholesterol in LDL-receptor knockout mice.

In another embodiment, any of the compounds described in U.S. Pat. No. 5,262,439 to Parthasarathy, incorporated by reference in its entirety, are used as LDL clearance drugs. The '439 patent describes probucol derivatives in which one or both of the hydroxyl groups are replaced with ester groups that increase the water solubility of the compound. In one embodiment, the derivative is selected from the group consisting of a mono- or di-probucol ester of succinic acid, glutaric acid, adipic acid, seberic acid, sebacic acid, azelaic acid, or maleic acid. In another embodiment, the probucol derivative is a mono- or di-ester in which the ester contains an alkyl or alkenyl group that contains a functionality selected from the group consisting of a carboxylic acid group, amine group, salt of an amine group, amide groups, amide groups, and aldehyde groups.

In another embodiment, any of the compounds described as "monoesters of probucol," as used in WO 98/09773, are used as LDL clearance drugs. A monoester of probucol includes (i) any monoester of probucol that is described in U.S. Pat. No. 5,262,439, for example, carboxylic acid esters and dicarboxylic acid esters and salts thereof; (ii) any monoester of probucol that has a greater solubility in water than probucol and which lowers plasma cholesterol, lowers LDL, and inhibits the expression of VCAM-1, as described in detail therein. In one embodiment, monoesters of probucol include dicarboxylic acid esters of probucol, including but not limited to the succinic acid, glutaric acid, adipic acid, suberic acid, sebacic acid, azelaic acid, and maleic acid esters. In another embodiment, the ester group includes a functional moiety which increases the solubility of the compound over probucol, including, but not limited to saturated and unsaturated dicarboxylic acids and salts thereof, amino carboxylic acids and salts thereof, aldehyde containing carboxylic acids and salts thereof, an amine group, a salt of an amine group, an amide group, aldehydes groups and the salts thereof. In yet another embodiment, the ester has a functional moiety selected from the group consisting of sulfonic acids, sulfonic acid esters, phosphoric acids, phosphoric acid esters, cyclic phosphates, polyhydroxyalkyl groups, carbohydrate group, C(O)-spacer-$SO_3H$, wherein spacer is —$(CH_2)_n$—, —$(CH_2)_n$—CO—, —$(CH_2)_n$—N—, —$(CH_2)_n$—O—, —$(CH_2)_n$—S—, —$(CH_2O)$—, —$(OCH_2)$—, —$(SCH_2)$—, —$(CH_2S$—), -(aryl-O)—, —(O-aryl)-, -(alkyl-O)—, —(O-alkyl)-; n is 0, 1, 2, 3, 4, 5, 6, 7, 8, 9, or 10; C(O)-spacer-$SO_3M$, wherein M is a metal used to form a pharmaceutically acceptable salt, for example, sodium or potassium, C(O)-spacer-$PO_3H_2$, C(O)-spacer-$PO_3M_2$, C(O)-spacer-$PO_3HM$, C(O)-spacer-$PO_4H$, C(O)-spacer-$PO_4M$, $SO_3M$, —$PO_3H_2$—$PO_3M_2$, —$PO_3HM$, cyclic phosphates, polyhydroxyalkyl, carbohydrate groups, C(O)-spacer-$[O(C_{1-3}$ alkyl)$_p]_n$, wherein n is as defined above and p is 1, 2, or 3, —$[O(C_{1-3}$ alkyl)$_p]_n$, carboxy lower alkyl, lower alkylcarbonyl lower alkyl, N,N-dialkyl amino lower alkyl, pyridyl lower alkyl, imidazolyl lower alkyl, morpholinyl lower alkyl, pyrrolidinyl lower alkyl, thiazolinyl lower alkyl, piperidinyl lower alkyl, morpholinyl lower hydroxyalkyl, N-pyrryl, piperazinyl lower alkyl, N-alkyl piperazinyl lower alkyl, triazolyl lower alkyl, tetrazolyl lower alkyl, tetrazolylamino lower alkyl, or thiazolyl lower alkyl.

In yet another embodiment, the compounds described in WO 98/09781 are used as LDL clearance enhancing drugs. These compounds include those of formula (I) or (II), or a pharmaceutically acceptable salt thereof, optionally in a pharmaceutically acceptable carrier. The compounds of formula (I) are

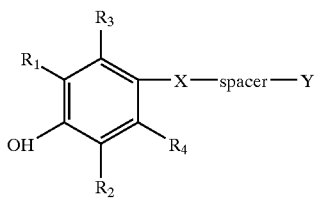

(I)

wherein

X is O, S, SO, $SO_2$, $CH_2$, or NH;

Spacer is a group selected from the group consisting of —$(CH_2)_n$—, —$(CH_2)_n$—, CO—, —$(CH_2)_n$—N—, —$(CH_2)_n$—O—, —$(CH_2)_n$—S—, —$(CH_2O)$—, —$(OCH_2)$—, —$(SCH_2)$—, —$(CH_2S$—), -(aryl-O)—, —(O-aryl)-, -(alkyl-O)—, —(O-alkyl)-;

n is 0, 1, 2, 3, 4, 5, 6, 7, 8, 9, or 10;

Y is substituted or unsubstituted aryl, substituted or unsubstituted heteroaryl, substituted or unsubstituted alkyl, substituted or unsubstituted alkoxy, substituted or unsubstituted alkoxyalkyl, substituted or unsubstituted alkylthio, substituted or unsubstituted alkylthioalkyl, substituted or unsubstituted alkylsulfinyl, substituted or unsubstituted alkylsulfinylalkyl, substituted or unsubstituted alkylsulfonyl, substituted or unsubstituted alkylsulfonylalkyl, $NH_2$, NHR, $NR_2$, $SO_2$—OH, OC(O)R, C(O)OH, C(O)OR, C(O)$NH_2$, C(O)NHR, C(O)$NR_2$, $SO_2NH_2$, $SO_2NHR$, $SO_2NR_2$;

R is alkyl, substituted alkyl, alkenyl, substituted alkenyl, alkynyl, substituted alkynyl, aryl, substituted aryl, alkyl-COOH, alkyl-COOalkyl, alkyl-COOaryl, heteroaryl, substituted heteroaryl, or when attached to a nitrogen atom, two adjacent R groups may combine to form a ring of 5 to 7 members;

$R^1$ and $R^2$ are independently straight chained, branched, or cyclic alkyl which may be substituted, aryl, substituted aryl, heteroaryl, substituted heteroaryl, alkaryl, or aralkyl; and wherein substituents on the $R^1$ or $R^2$ groups are selected from the group consisting of hydrogen, halogen, alkyl, nitro, amino, alkylamino, dialkylamino, acyl, and acyloxy;

$R^3$ and $R^4$ are independently any group that does not otherwise adversely affect the desired properties of the molecule, including H, halogen, or $R^1$.

The compound of formula (II) has the following structure

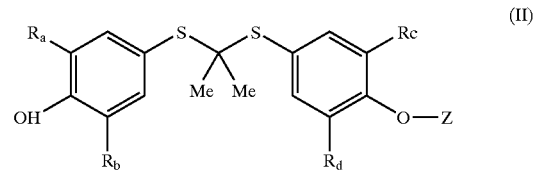

(II)

wherein $R_a$, $R_b$, $R_c$, and $R_d$ are independently any group that does not otherwise adversely affect the desired properties of the molecule, including hydrogen, straight chained, branched, or cyclic alkyl which may be substituted, aryl, substituted aryl, heteroaryl, substituted heteroaryl, alkaryl, substituted alkaryl, aralkyl or substituted aralkyl; substituents on the $R_a$, $R_b$, $R_c$ and $R_d$ groups are selected from the group consisting of hydrogen, halogen, alkyl, nitro, amino, haloalkyl, alkylamino, dialkylamino, acyl, and acyloxy;

Z is selected from the group consisting of hydrogen, alkyl, substituted alkyl, alkenyl, substituted alkenyl, alkynyl, substituted alkynyl, aryl, aralkyl, alkaryl, heteroaryl, heteroaralkyl, a carbohydrate group, —$(CH_2)$—$R_e$, —C(O)—$R_g$, and —C(O)—$(CH_2)_n$—$R_h$, wherein (a) when each of $R_a$, $R_b$, $R_c$, and $R_d$ are t-butyl, Z cannot be hydrogen and (b) when each of $R_a$, $R_b$, $R_c$, and $R_d$ are t-butyl, Z cannot be the residue of succinic acid;

$R_e$ is selected from the group consisting of alkyl, substituted alkyl, alkenyl, substituted alkenyl, alkynyl, substituted alkynyl, alkoxy, substituted alkyloxy, alkoxyalkyl, substituted alkoxyalkyl, $NH_2$, NHR, $NR_2$, mono- or polyhydroxy-substituted alkyl, aryl, substituted aryl, heteroaryl, substituted heteroaryl, acyloxy, substituted acyloxy, COOH, COOR, —CH(OH)$R_k$, hydroxy, C(O)$NH_2$, C(O)NHR, C(O)$NR_2$;

$R_g$ is selected from the group consisting of alkyl, substituted alkyl, alkenyl, substituted alkenyl, alkynyl, substituted alkynyl, alkoxy, substituted alkyloxy, alkoxyalkyl, substituted alkoxyalkyl, $NH_2$, NHR, $NR_2$, mono- or polyhydroxy-substituted alkyl, aryl, substituted aryl, heteroaryl, substituted heteroaryl;

$R_h$ is selected from the group consisting of alkyl, substituted alkyl, alkenyl, substituted alkenyl, alkynyl, substituted alkynyl, alkoxy, substituted alkyloxy, alkoxyalkyl, substituted alkoxyalkyl, $NH_2$, NHR, $NR_2$, mono- or polyhydroxy-substituted alkyl, aryl, substituted aryl, heteroaryl, substituted heteroaryl, acyloxy, substituted acyloxy, COOH, COOR, —CH(OH)$R_k$, hydroxy, O-phosphate, $C(O)NH_2$, C(O)NHR, C(O) $NR_2$ and pharmaceutically acceptable salts thereof;

Or, in an alternative embodiment, $R_e$, $R_g$, and $R_h$ can independently be a substituent which improves the water solubility of the compound, including, but not limited to C(O)-spacer-$SO_3$H, wherein spacer is as defined above, C(O)-spacer-$SO_3$M, wherein M is a metal used to form a pharmaceutically acceptable salt, for example, sodium, C(O)-spacer-$PO_3H_2$, C(O)-spacer-$PO_3M_2$, C(O)-spacer-$PO_3$HM, C(O)-spacer-$PO_4$H, C(O)-spacer-$PO_4$M, $SO_3$M, —$PO_3H_2$, —$PO_3M_2$, —$PO_3$HM, cyclic phosphates, polyhydroxyalkyl, carbohydrate groups, C(O) spacer-$[O(C_{1-3}$ alkyl$)_p]_n$, wherein n is as defined above and p is 1, 2, or 3, —$[O(C_{1-3}$ alkyl$)_p]_n$, carboxy lower alkyl, lower alkylcarbonyl lower alkyl, N,N-dialkyl amino lower alkyl, pyridyl lower alkyl, imidazolyl lower alkyl, morpholinyl lower alkyl, pyrrolidinyl lower alkyl, thiazolinyl lower alkyl, piperidinyl lower alkyl, morpholinyl lower hydroxyalkyl, N-pyrryl, piperazinyl lower alkyl, N-alkyl piperazinyl lower alkyl, triazolyl lower alkyl, tetrazolyl lower alkyl, tetrazolylamino lower alkyl, or thiazolyl lower alkyl.

II. Combination or Alternation Therapy

In still another embodiment of the present invention, a method is provided for lowering cholesterol in humans comprising administering to a patient in need thereof an effective amount of a compound that binds to cholesterol-carrying lipoprotein (e.g. LDL or VLDL) in a manner that alters the three dimensional configuration of the lipoprotein and increases the binding affinity of the apoB-100 protein to the LDL receptors on the surface of hepatic cells in combination or alternation with a drug that lowers cholesterol via a different biological pathway, to provide augmented results.

In one aspect, the second cholesterol lowering agent is a statin. The combination of the LDL clearance enhancing drug with a statin creates a synergistic or augmented lowering of LDL, because statins lower cholesterol by a different mechanism, i.e., by inhibiting of 3-hydroxy-3-methylglutaryl coenzyme A (HMG CoA) reductase, a key enzyme in the cholesterol biosynthetic pathway. The statins decrease liver cholesterol biosynthesis, which increases the production of LDL receptors thereby decreasing plasma total and LDL cholesterol (Grundy S. M. New Engl. J. Med. (1988) 319: 24–32. and Endo A: J. Lipid Res. (1992) 33: 1569–1582). Depending on the agent and the dose used, statins may decrease plasma triglyceride levels and may increase HDL. Currently the statins on the market are Lovastatin (Merck), Simvastatin (Merck), Pravastatin (Sankyo and Squibb) and Fluvastatin (Sandoz). A fifth statin, Atorvastatin (Parke-Davis/Pfizer), is the most recent entrant into the statin market. Any of these statins can be used in combination with the LDL clearance enhancing drug.

In other embodiments, the LDL clearance enhancing drug is administered in an effective combination or alternation with a bile acid sequestrant, nicotinic acid (niacin), probucol, a fibrate derivative (bezafibrate, fenofibrate, gemfibrozil, and clofibrate), Neomycin, or cholestyramine.

III. Assays

The invention includes assays to determine (i) whether the binding of a potential LDL clearance drug to LDL or VLDL can cause a change in the conformation of apoB-100 which would affect LDL-receptor binding; and (ii) a method to determine whether the complex of a potential LDL clearance enhancing drug changes the electrophorectic mobility pattern of LDL or VLDL, and if so, whether the interaction alters the structure of apoB-100 present on LDL or VLDL.

EXAMPLE 1

The Monosuccinic Acid Ester of Probucol Binds to VLDL and LDL In Vivo and In Vitro To examine if the monosuccinic acid ester of probucol partitions with plasma circulating lipoproteins, rabbits were fed a high-fat diet for six weeks and dosed with the compound at a dose of 150 mg/Kg per day orally. The animals were bled at six weeks and plasma lipoproteins isolated at high-speed using ultra-centrifugation.

Whole plasma was fractionated by fast phase liquid chromatography (FPLC) using a Superose 6HR 10/30 column. Elution was performed in a phosphate-buffered saline solution containing 0.01% EDTA and 0.02% $NaN_3$ at a flow rate of 0.3 m/min. Approximately 0.6 ml was collected for each fraction and 20 fractions were available for analysis. The cholesterol content of the peaks corresponding to low density lipoprotein (LDL) and high density lipoprotein (HDL) were compared to CDC reference methods. VLDL corresponds to fractions 4–8 (elution volumes 7.2–9.6), LDL to fractions 9–16 (elution volume 10.2–14.4) and HDL to fractions 17–23 (elution volume 15–18.6).

The monosuccinic acid ester of probucol (MSE) levels in the different lipoprotein fractions were determined by high pressure liquid chromatography (HPLC) using a Rainin C 18 column (830201-C). Fractions corresponding to the different lipoprotein fractions were pooled and dried down by centrifugation under vacuum and resuspended in 0.5 ml of phosphate buffered saline. MSE was extracted with 0.5 ml of ether. 100 ul of the ether solution was added to 400 ul of acetonitrile and 0.02 ml was loaded onto the column. The mobile phase was 75:20:5 acetonitrile, methanol, and 50 mM acetic acid in methanol.

The amount of the MSE bound to each of the lipoproteins was estimated. FIG. 1 is a bar graph of the distribution of the monosuccinic acid ester ("MSE") of probucol in circulating lipoproteins. Most (>80%) of the MSE was recovered in the different lipoprotein fractions, with most being found in the VLDL fraction, followed by LDL and some in IDL and HDL. Very little of the monosuccinic acid ester of probucol was found in the non-lipoprotein plasma fraction. This data demonstrates that the monosuccinic acid ester of probucol partitions with circulating plasma lipoproteins mainly, the VLDL and the LDL fractions.

EXAMPLE 2

In order to demonstrate the binding of the monosuccinic acid ester of probucol to purified human LDL in vitro, agarose electrophoresis was employed. Agarose electrophoresis is a technique used to separate and study lipoproteins. The monosuccinic acid ester of probucol was added to purified human LDL and the mixture was run on agarose electrophoresis. Addition of the probucol derivative to LDL shifted the mobility of LDL, suggesting an interaction of the monosuccinic acid ester of probucol with LDL, most likely a physical association of the compound with the lipoprotein. In contrast, probucol did not shift the mobility of LDL.

EXAMPLE 3

The Monosuccinic Acid Ester of Probucol Binds to LDL and Changes the Epitope Expression of LDL-apoB-100

To determine if the binding of the monosuccinic acid ester to VLDL and LDL can cause a change in the structure of apoB-100, an immunoreactivity assay was designed. This is a sandwich ELISA assay which measures the expression of a specific epitope on apoB-100. Essentially the sandwich ELISA consists of a specific monoclonal antibody directed to that epitope on apoB-100 as a capture antibody laid onto a microtitre plate. LDL or VLDL added to the plate is bound to the antibody as a result of recognition of the specific epitope. A second polyclonal antibody is then used to quantify the amount of LDL captured.

The detailed immunoreactivity protocol is as follows. A nunc maxi-sorp microtiter plate is coated overnight at 4° C. with 100 µl of Anti-Human ApoB monoclonal antibody from Boehringer Mannheim (catalog # 1533 975) diluted 1:1000 in PBS pH 7.4. The compounds are dissolved in DMSO with appropriate concentration of LDL for 15 minutes and incubated at 37° C.

The coated microtiter plate is washed three times with 200 µl PBS/0.05% tween, and a sample of 100 µl LDL/Compound or LDL standard is added to each well. The plates are then incubated for 2 hours at room temperature.

The microtiter plate is washed three times with 200 µl PBS/0.05% tween, and 100 µl of 1:2000 Polyclonal Human Anti-ApolipoproteinB from Boehringer Mannheim (catalog # 726 494) in PBS/tween 0.05% is added. The plate is incubated for one hour at room temperature.

The microtiter plate is washed three times with 200 ul PBS/0.05% tween, and 100 µl of 1:2000 Anti-Sheep Ig peroxidase from Boehringer Mannheim (catalog # 605 345) in PBS/05% tween is added. The plate is incubated for one hour at room temperature.

The microtiter plate is washed three times with 200 ul PBS/0.05% tween, and 100 µl of TMB substrate is added and incubated for 5–10 minutes in the dark. The reaction is stopped with 15 µl 8N $H_2SO_4$ and read on the Bio-Rad Microplate plate reader at 450 nm within 30 minutes.

As shown in FIG. 6a, incubation with several probucol derivatives and vitamin E succinate increased the binding of LDL to the capture monoclonal antibody. In contrast, probucol, succinate and vitamin E had no significant effect on LDL binding. This data indicates that certain compounds including the monosuccinic acid ester of probucol, which increased binding by 300% at 15 uM and 500% at 30 uM, can alter the expression of a specific epitope on apoB-100 and increase the binding of LDL to the monoclonal antibody directed to that epitope.

Figure 6B:
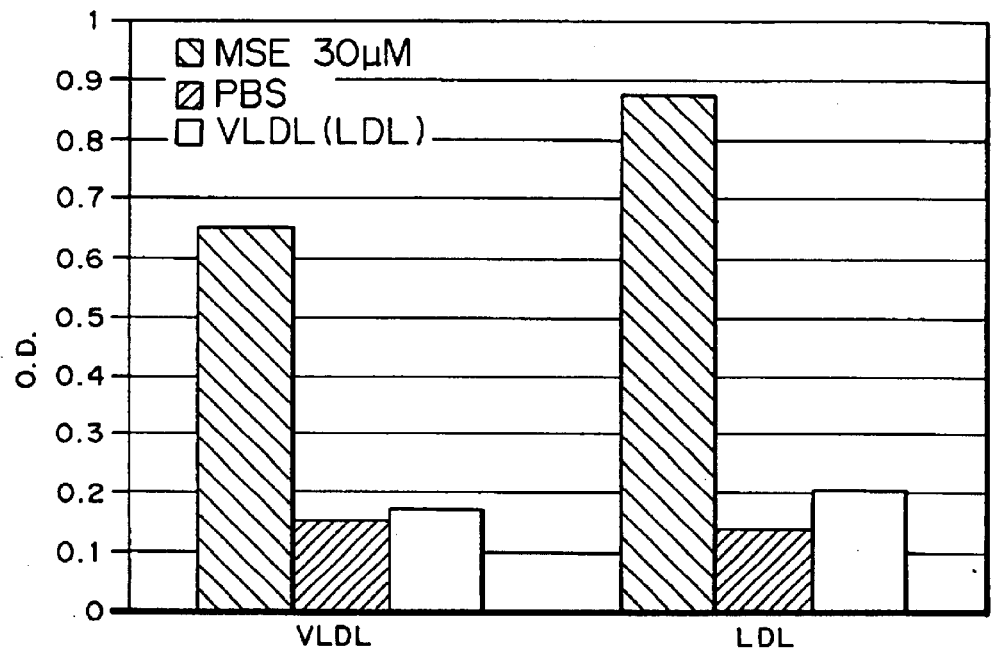
FIG. 6b is a graph that demonstrates the increased binding of the apoB-100 epitope in VLDL to the monoclonal antibody for the monosuccinic acid ester of probucol relative to the native VLDL.

As shown in FIG. 6b, the monosuccinic acid ester of probucol similarly enhances the apoB-100 epitope in VLDL and increases binding to the antibody by about 375% relative to the native VLDL.

EXAMPLE 4

The Monosuccinic Acid Ester of Probucol Enhances the Uptake of LDL by Liver Cells (HepG2) in Culture In order to test whether the change in structure of LDL by the monosuccinic acid ester of probucol can affect the uptake of this lipoprotein by liver cells in vitro, purified human radioiodinated LDL was mixed with various concentrations of the probucol derivative and incubated for 15 minutes at room temperature. After that, the mixture of LDL and the probucol derivative was added to HepG2 cells in culture and the uptake of radiolabeled LDL measured after 24 h. At each concentration of compound, the specific uptake of LDL was also determined by examining LDL uptake in the presence of excess unlabeled LDL.

Figure 3:
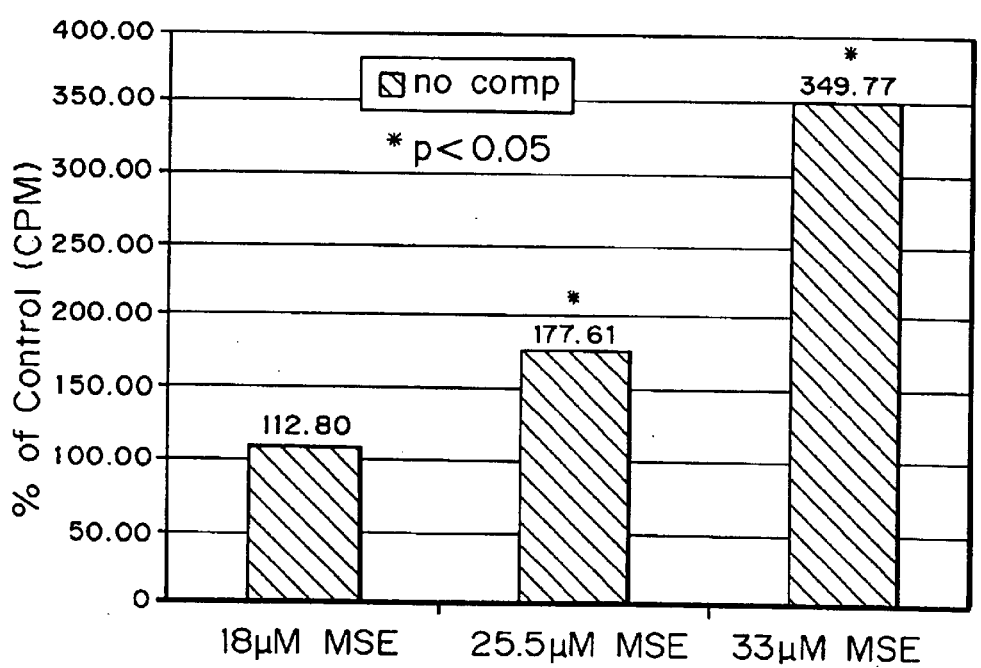
FIG. 3 is a bar chart graph of the effect of MSE on the uptake of 125I-LDL in HepG2 cells at 18, 25.5 and 33 µM concentrations. As indicated, MSE increased the uptake of radiolabeled LDL in the HepG2 cells in a dose dependent fashion.
Figure 2:
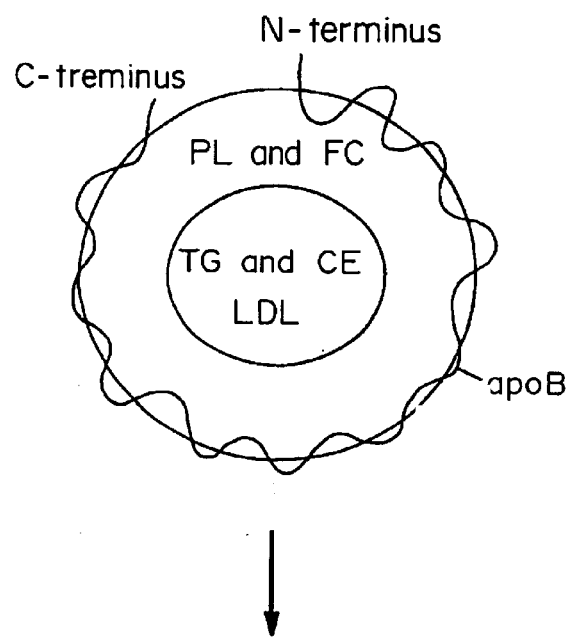
FIG. 2 is an illustration of the changes in the presentation of the epitope of LDL-apoB-100 before and after complexation with MSE.
Figure 2:
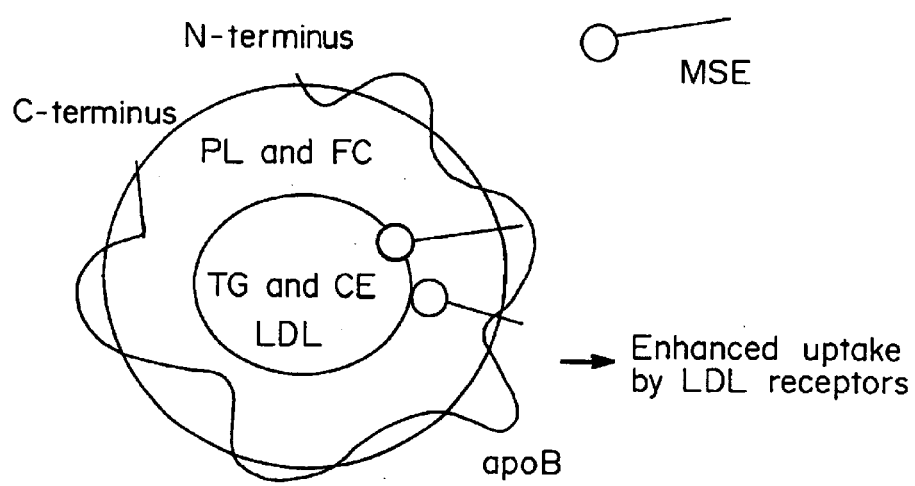
Figure 4:
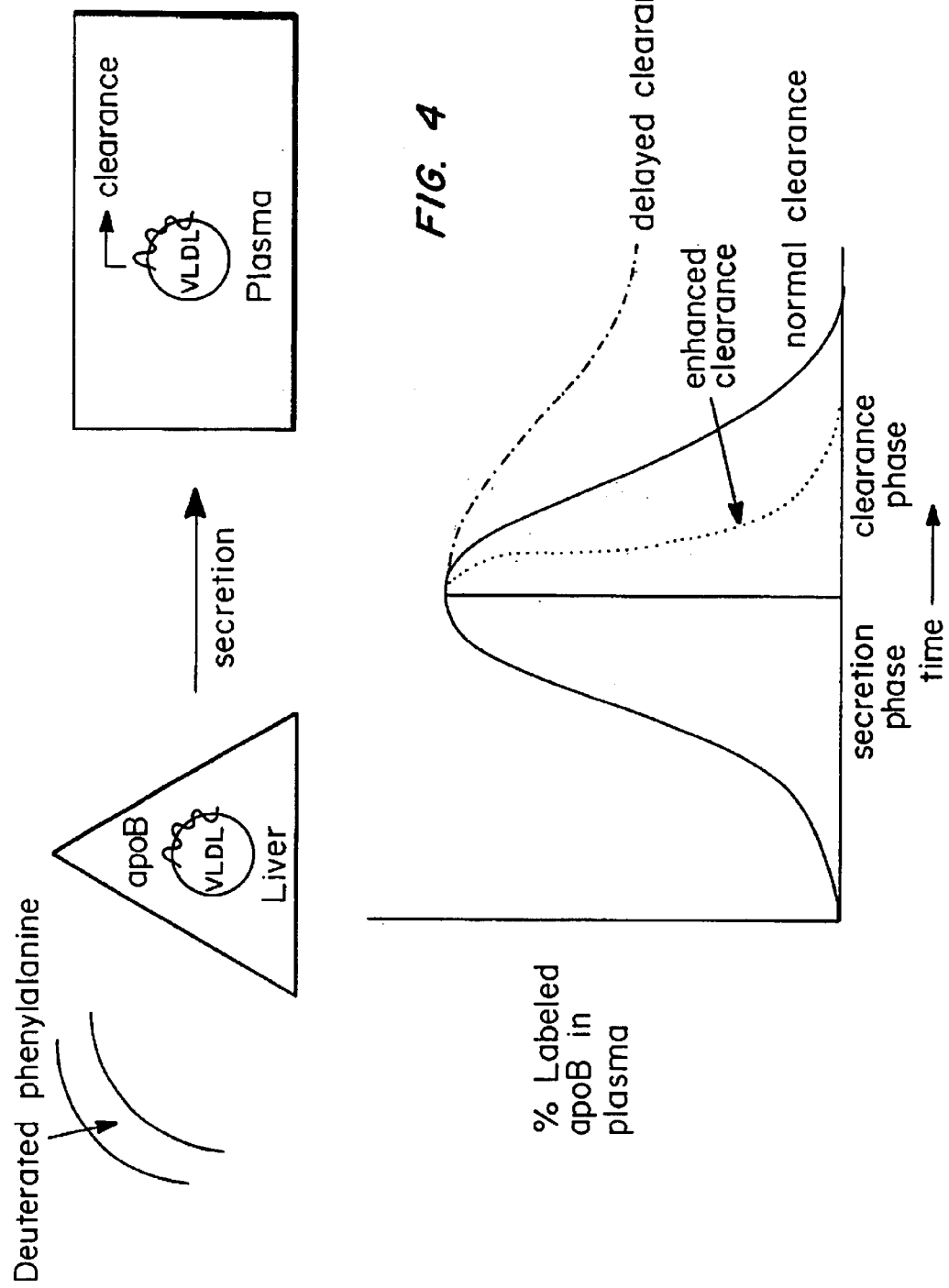
FIG. 4 is an illustration of VLDL turnover studies using the stable isotope technique as well as a graph of the percent labeled apoB in plasma as a function of time over the secretion phase and the clearance phase. The graph illustrates enhanced clearance, normal clearance, and delayed clearance patterns of apoB over time.

As shown in FIG. 3, the monosuccinic acid ester of probucol increased specific uptake of LDL at 18, 25.5 and 33 uM concentrations by 12.8, 77.6 and 249%, respectively, relative to LDL uptake in the absence of MSE. These data demonstrate that addition of monosuccinic acid ester of probucol to human LDL causes concentration dependent increase in uptake of LDL by the cells.

EXAMPLE 5

The Structural Changes in ApoB-100 Caused by the Monosuccinic Acid Ester of Probucol may be Highly Specific and not a Global Change in apoB-100

Figure 7:
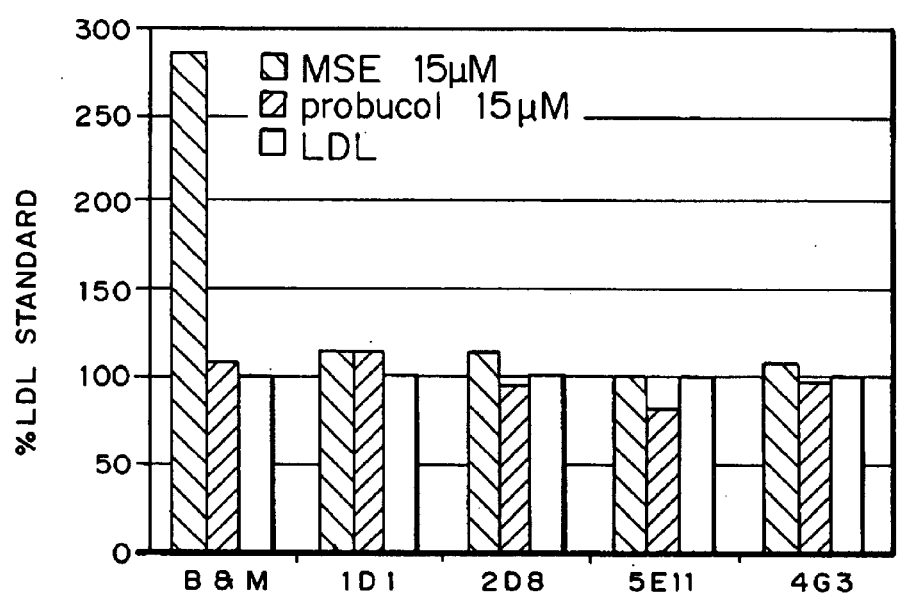
FIG. 7 is a graph that demonstrates the specificity of epitope expression changes by the monosuccinic acid ester of probucol by comparing its effects on four other monoclonal antibodies with the Boehringer Mannheim antibody.

The specificity of epitope expression changes by the monosuccinic acid ester of probucol were established by examining MSE's effects on other epitopes on LDL. This was probed by using four other monoclonal antibodies (1D, 2D8, 5E11, 4G3) in comparison to the Boehringer Mannheim (Band M) antibody used in the assays described above. As shown in FIG. 7, the epitope expression detected by the Band M antibody on LDL was significantly enhanced by the monosuccinic acid ester of probucol and the expression of epitopes detected by the other four antibodies against apoB-100 was unaffected by MSE. These data demonstrate that the structural changes in apoB-100 caused by MSE may be highly specific and not a global change in apoB-100.

EXAMPLE 6

Figure 5A:
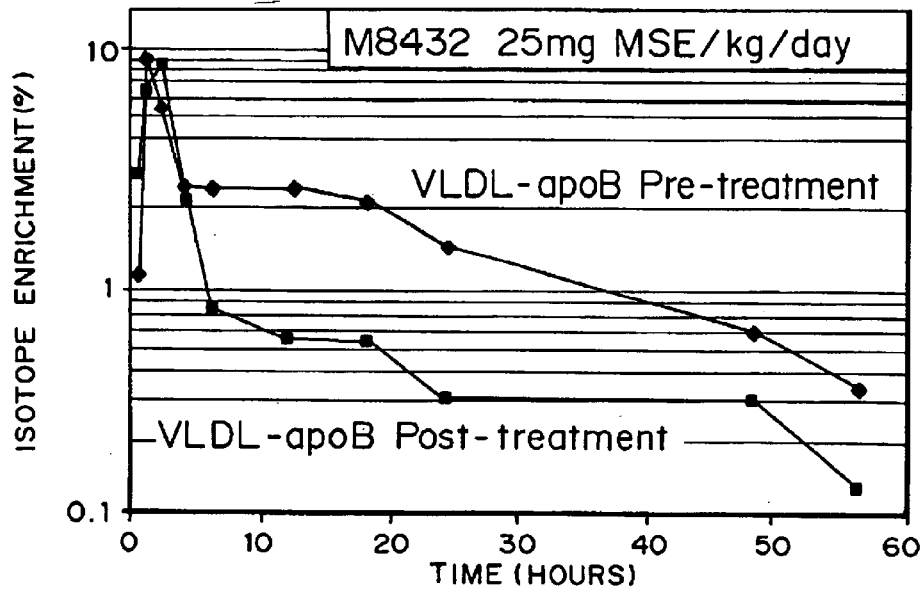
FIGS. 5a and 5b are graphs that compare the enhanced clearance rate of VLDL from the plasma component of monkeys dosed with 25 mg/kg/day of the monosuccinic acid ester of probucol compared to the untreated clearance rate.
Figure 5B:
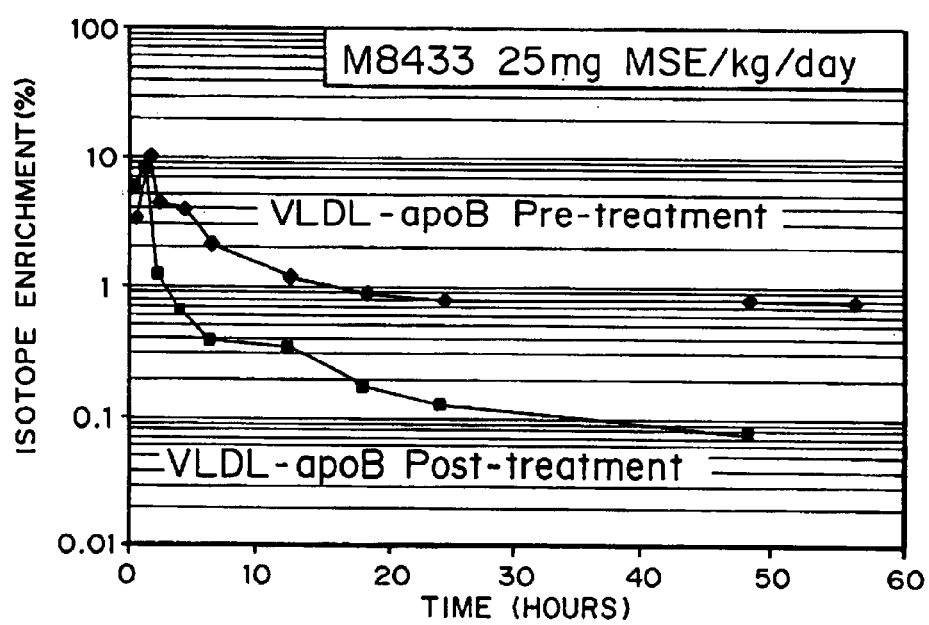

The Monosuccinic Acid Ester of Probucol Increases the Clearance Rates of VLDL and LDL and Lowers their Plasma Concentration in Monkey Model A lipoprotein turnover study was performed in monkeys that were dosed with the monosuccinic acid ester of probucol (25 mg/kg/day for one four weeks). The clearance rates of VLDL and LDL were examined before and after treatment of the animals using a stable isotope technique to label apoB-100 in VLDL and LDL. As shown in FIGS. 5a and 5b, there was a marked enhancement in the clearance of VLDL after treatment with of the animals with the probucol derivative relative to before dosing. Similarly, LDL clearance rates were also increased by treatment with the monosuccinic acid ester of probucol. There were no apparent effects of the probucol derivative on the production of VLDL or LDL. These data demonstrate that treatment with the monosuccinic acid ester of probucol enhances the clearance rate of VLDL and LDL.

EXAMPLE 7

The Monosuccinic Acid Ester of Probucol Requires Functional LDL Receptors for its Lipid Lowering Effects The data presented above suggest that the monosuccinic acid ester of probucol binds to LDL particles, increases cellular uptake of LDL and thereby increases the clearance rate of LDL from the plasma. To explore whether the enhanced clearance is mediated by the tissue LDL receptors, the major clearance mechanism for LDL in the body, the LDL lowering activity of the monosuccinic acid ester of probucol was tested in a mouse model that lacks functional LDL receptors (eliminated through genetic engineering). Oral treatment of mice with the monosuccinic acid ester of probucol (150 mg/kg/day) mixed together with high fat/high cholesterol diet for 12 weeks did not result in any significant effects on total plasma cholesterol levels. In contrast probucol administered similarly at the same dose lowered plasma cholesterol moderately (17%) but statistically significantly. These data demonstrate that functional LDL receptors are required for cholesterol lowering by the monosuccinic acid ester of probucol but not for lipid lowering by probucol.

EXAMPLE 8

Correlation of Cell Free Assay with Cholesterol Lowering

The monosuccinic acid ester of probucol and several other compounds were tested in vitro in the immunoreactivity cell-free assay described above in Example 3 and in vivo in hamsters for their ability to lower plasma cholesterol. The results are provided in Table 1.

TABLE 1

| Compounds | Cell-Free Assay | Hamster |
|---|---|---|
| Butanedioic acid, mono[4-[[1-[[3,5-bis(1,1-dimethylethyl)-4-hydroxyphenyl]thio]-1-methylethyl]thio]-2,6-bis(1,1-dimethylethyl)phenyl] ester (MSE) | yes | yes |
| pentanedioic acid, mono[4-[[1-[3,5-bis(1,1-dimethylethyl)-4-hydroxyphenyl]thio]1-methylethyl]thio-2,6-bis(1,1-dimethylethyl)phenyl]ester | yes | yes |
| 2,6-di-tert-butyl-4-thio-(4'-(trifluoromethyl)benzyl) phenol | yes | yes |
| 2,6-di-tert-butyl-4-thio-(4'-methyl-N,N-dimethylbenzenesulfonamide) phenol | yes | yes |
| 6-deoxy-6-(probucol-1-yl)-D-glucose | yes | yes |
| probucol-2,3,4,5,6-pentahydroxyhexyl ether | yes | yes |
| 2,6-di-tert-butyl-4-thio-(4'-(methyl)phenylethyl alcohol))phenol | yes | yes |
| 4-[(3,5-di-tert-butyl-4-hydroxyphenylthio)methyl]phenyl benzoate | yes | yes |
| N,N-dimethyl-4-[(3,5-di-tert-butyl-4-hydroxyphenylthio)methyl]phenylacetamide | yes | yes |
| Methyl 5-(3,5-id-tert-butyl-4-hydroxyphenylthio)methyl-2-furoate | yes | yes |
| α-(3,5-di-tert-butyl-4-hydroxyphenylthio)-4-nitro-acetophenone | no | yes |
| N,N-dimethyl-4-[(3,5-di-tert-butyl-4-hydroxyphenylthio)methyl]benzamide | no | yes |
| 2,6-di-tert-butyl-4-[(3-trifluoromethyl)benzylthio]phenol | no | yes |
| Mono[4-(3,5-di-tert-butyl-4-hydroxybenzyl)2,6-di-tert-butylphenyl] succinate | yes | no |
| Mono[4-(3,5-di-tert-butyl-4-hydroxyphenacylthio)-2,6-di-tert-butylphenyl] succinate | yes | no |
| 5-[4-[[1-[[3,5-bis(1,1-dimethylethyl))-4-hydroxyphenyl)thio]-1-methylethyl]thioo-2,6-bis(1,1-dimethylethyl)phenoxy-2,3,4-trihydroxy-pentanoic acid | yes | no |
| 2,6-di-tert-butyl-4-[(2,4-dinitrobenzyl)thio]phenol | no | no |
| 2,6-di-tert-butyl-4-[(4-fluorobenzyl)thio]phenol | no | no |
| N,N-diethyl-4-[3,5-di-tert-butyl-4-hydroxyphenylthio)methyl]benzene-sulfonamide | no | no |
| 2,6-di-tert-butyl-4-[4-fluoro-2-(trifluoromethyl)benzylthio]phenol | no | no |
| N,N-dipropyl-4-[(3,5-di-tert-butyl-4-hydroxyphenylthio)methyl]benzamide | no | no |
| 2,6-di-tert-butyl-4-[(3-trifluoromethoxy)benzylthio]phenol | no | no |
| Mono[4-(3,5-di-tert-butyl-4-hydroxybenzyl)-2,6-di-tert-butylphenyl]glutarate | no | no |

IV. Pharmaceutical Compositions

Humans, equine, canine, bovine and other animals, and in particular, mammals, can be treated for cholesterolemia by administering to the patient an effective amount of one or more of the above-identified compounds or a pharmaceutically acceptable derivative or salt thereof in a pharmaceutically acceptable carrier or diluent. The active materials can be administered by any appropriate route, for example, orally, parenterally, intravenously, intradermally, subcutaneously, or topically.

As used herein, the term pharmaceutically acceptable salts or complexes refers to salts or complexes that retain the desired biological activity of the above-identified compounds and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; (b) base addition salts formed with polyvalent metal cations such as zinc, calcium, bismuth, barium, magnesium, aluminum, copper, cobalt, nickel, cadmium, sodium, potassium, and the like, or with an organic cation formed from N,N-dibenzylethylene-diamine, D-glucosamine, ammonium, tetraethylammonium, or ethylenediamine; or (c) combinations of (a) and (b); e.g., a zinc tannate salt or the like.

The active compound is included in the pharmaceutically acceptable carrier or diluent in an amount sufficient to deliver to a patient a therapeutically effective amount without causing serious toxic effects in the patient treated. A preferred dose of the active compound for all of the above-mentioned conditions is in the range from about 0.1 to 500 mg/kg, preferably 1 to 100 mg/kg per day. The effective dosage range of the pharmaceutically acceptable derivatives can be calculated based on the weight of the parent compound to be delivered. If the derivative exhibits activity in itself, the effective dosage can be estimated as above using the weight of the derivative, or by other means known to those skilled in the art.

For systemic administration, the compound is conveniently administered in any suitable unit dosage form, including but not limited to one containing 1 to 3000 mg, preferably 5 to 500 mg of active ingredient per unit dosage form. A oral dosage of 25–250 mg is usually convenient. The active ingredient should be administered to achieve peak plasma concentrations of the active compound of about 0.1 to 100 mM, preferably about 1–10 mM. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The active compound or pharmaceutically acceptable salt or derivative thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable derivatives or salts thereof can also be administered with other active materials that do not impair the desired action, or with materials that supplement the desired action, such as antibiotics, antifungals, antiinflammatories, or antiviral compounds. The active compounds can be administered with lipid lowering agents such as probucol and nicotinic acid; platelet aggregation inhibitors such as aspirin; antithrombotic agents such as coumadin; calcium channel blockers such as varapamil, diltiazem, and nifedipine; angiotensin converting enzyme (ACE) inhibitors such as captopril and enalopril, and β-blockers such as propanalol, terbutalol, and labetalol. The compounds can also be administered in combination with nonsteroidal antiinflammatories such as ibuprofen, indomethacin, aspirin, fenoprofen, mefenamic acid, flufenamic acid, sulindac. The compound can also be administered with corticosteriods.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

Suitable vehicles or carriers for topical application are known, and include lotions, suspensions, ointments, creams, gels, tinctures, sprays, powders, pastes, slow-release transdermal patches, aerosols for asthma, and suppositories for application to rectal, vaginal, nasal or oral mucosa.

Thickening agents, emollients, and stabilizers can be used to prepare topical compositions. Examples of thickening agents include petrolatum, beeswax, xanthan gum, or polyethylene glycol, humectants such as sorbitol, emollients such as mineral oil, lanolin and its derivatives, or squalene. A number of solutions and ointments are commercially available.

Natural or artificial flavorings or sweeteners can be added to enhance the taste of topical preparations applied for local effect to mucosal surfaces. Inert dyes or colors can be added, particularly in the case of preparations designed for application to oral mucosal surfaces.

The active compounds can be prepared with carriers that protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Many methods for the preparation of such formulations are patented or generally known to those skilled in the art.

If administered intravenously, preferred carriers are physiological saline or phosphate buffered saline (PBS).

The active compound can also be administered through a transdermal patch. Methods for preparing transdermal patches are known to those skilled in the art. For example, see Brown, L., and Langer, R., Transdermal Delivery of Drugs, Annual Review of Medicine, 39:221–229 (1988), incorporated herein by reference.

In another embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylacetic acid. Methods for preparation of such formulations will be apparent to those skilled in the art. The materials can also be obtained commercially from Alza Corporation and Nova Pharmaceuticals, Inc. Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives are then introduced into the container. The container is then swirled by hand to free lipid material from the sides of the container and to disperse lipid aggregates, thereby forming the liposomal suspension.

Modifications and variations of the present invention will be obvious to those skilled in the art from the foregoing. All of these embodiments are considered to fall within the scope of this invention.

We claim:

1. A method to determine if a compound causes a change in the structure of apolipoprotein B-100 in a cholesterol-containing low density lipoprotein thus increasing the binding of an epitope on the apolipoprotein B-100 to the LDL-receptor, comprising:
   (i) mixing the compound with and allowing it to bind to cholesterol-containing low density lipoprotein forming a complex;
   (ii) exposing the complex to a first capture antibody that is attached to a solid phase material and is directed to the epitope on apolipoprotein B-100 that binds to the LDL-receptor, forming a combination;

(iii) adding a second antibody which binds to the combination;

(iv) detecting the second antibody bound to the combination by the addition of a third antibody that binds the second antibody and to which is attached a label;

(v) quantifying the amount of the captured complex by quantifying the amount of label; and (vi) comparing the amount of cholesterol-containing low density lipoprotein captured by the assay to a control, wherein an increase in the amount of cholesterol-containing low density lipoprotein captured indicates a change in the structure of apoB-100 in the cholesterol-containing low density lipoprotein, thus increasing binding to the low density lipoprotein receptor.

2. The method of claim 1, wherein the control is low density lipoprotein in the absence of test compound.

3. A method for assessing whether a compound first binds to a cholesterol-containing lipoprotein, enhancing the binding of the cholesterol-containing lipoprotein to a low density lipoprotein hepatic receptor and thus lowering plasma cholesterol, the method comprising:

(a) allowing the compound to form a complex with a cholesterol-containing lipoprotein in vivo, (b) isolating the resulting complex, and (c) determining whether the formation of the complex causes a change in the three dimensional conformation of apoB-100 in the cholesterol-containing lipoprotein that enhances the binding of the lipoprotein to the LDL hepatic receptor.

4. The method of claim 3, wherein the formation of the complex is determined by a sandwich immunoreactivity assay.

5. The method of claim 3, wherein the formation of the complex is determined using agarose electrophoresis.

6. The method of claim 3, wherein the cholesterol-containing low-density lipoprotein is LDL.

7. The method of claim 3, wherein the cholesterol-containing low-density lipoprotein is VLDL.

8. A method to determine if a compound causes a change in the structure of apolipoprotein B-100 in a cholesterol-containing low density lipoprotein thus increasing the binding of an epitope on the apolipoprotein B-100 to an LDL-receptor, comprising:

(i) mixing the compound with and allowing it to bind to cholesterol-containing low density lipoprotein forming a complex;

(ii) exposing the complex to a first capture antibody that is attached to a solid phase material and is directed to the epitope on apolipoprotein B-100 that binds to the LDL-receptor, forming a combination;

(iii) adding to the combination a second antibody which binds the apoB-100 in the combination and to which is attached a label;

(iv) quantifying the amount of the captured complex by quantifying the amount of label; and (v) comparing the amount of cholesterol-containing low density lipoprotein quantified in step (iv) to a control, wherein an increase in the amount of cholesterol-containing low density lipoprotein captured indicates a change in the structure of apoB-100 in the cholesterol-containing low density lipoprotein, thus increasing binding to the low density lipoprotein receptor.

9. The method of claim 8, wherein the control is low density lipoprotein in the absence of test compound.

* * * * *